United States Patent
Korte

(10) Patent No.: US 7,306,949 B2
(45) Date of Patent: Dec. 11, 2007

(54) COMBINATION OF CRP AND D-DIMER FOR IN VITRO DIAGNOSIS OF DEEP VENOUS THROMBOSIS (DVT)

(75) Inventor: Wolfgang Korte, St. Gallen (CH)

(73) Assignee: Dade Behring Marburg GmbH, Marburg (DE)

( * ) Notice: Subject to any disclaimer, the term of this patent is extended or adjusted under 35 U.S.C. 154(b) by 578 days.

(21) Appl. No.: 10/636,578

(22) Filed: Aug. 8, 2003

(65) Prior Publication Data

US 2004/0029286 A1 Feb. 12, 2004

(30) Foreign Application Priority Data

Aug. 9, 2002 (EP) ................... 02017913

(51) Int. Cl.
*G01N 33/00* (2006.01)
*G01N 33/48* (2006.01)

(52) U.S. Cl. .......... 436/86; 436/63; 436/518; 436/533; 436/811

(58) Field of Classification Search ............ 436/86, 436/811, 63, 518, 533
See application file for complete search history.

(56) References Cited

OTHER PUBLICATIONS

Jossang, Bjarne et al. "C-reactive protein & D-dimer in the diagnosis of deep venous thrombosis," Tidsskrift for den Norske Laegeforening, 1992, vol. 112, No. 9, pp. 1153-1155 (abstract).*
Roberts et al. Clinical Chemistry, vol. 46, No. 4, 2000, pp. 461-468.*
Janssen et al. (abstract) Thrombosis and Haemostasis, vol. 77, No. 2, Feb. 1997, pp. 262-266.*
Bucek, R. et al., "C-reactive protein in the diagnosis of deep vein thrombosis", British Journal of Haematology, vol. 119, pp. 385-389, (2002).
Horney et al., "Evaluation of analyses to exclude suspected thrombosis. Don't rely on the D-dimer test!", Lakartidingen. Sweden 7, vol. 95, No. 1-2, pp. 55-58, Jan. 7, 1998.
English-language translation of: B. Jossang et al., *Tidsskr Nor Laegeforen* [Journal of the Norwegian Medical Society], 112(9):1153-5 (1992).
M.C.H. Janssen et al., *Thrombosis and Haemostasis* 77(2): 262-266 (1997).

* cited by examiner

*Primary Examiner*—Maureen M. Wallenhorst
(74) *Attorney, Agent, or Firm*—Finnegan, Henderson, Farabow, Garrett and Dunner, L.L.P.

(57) ABSTRACT

The present invention relates to an in vitro diagnostic method for patients with suspected deep venous thrombosis wherein by combined testing of patients' samples for D-dimer and CRP both the sensitivity and the negative predictive value of DVT diagnostics can be increased up to 100%.

7 Claims, 1 Drawing Sheet

Figure 1:
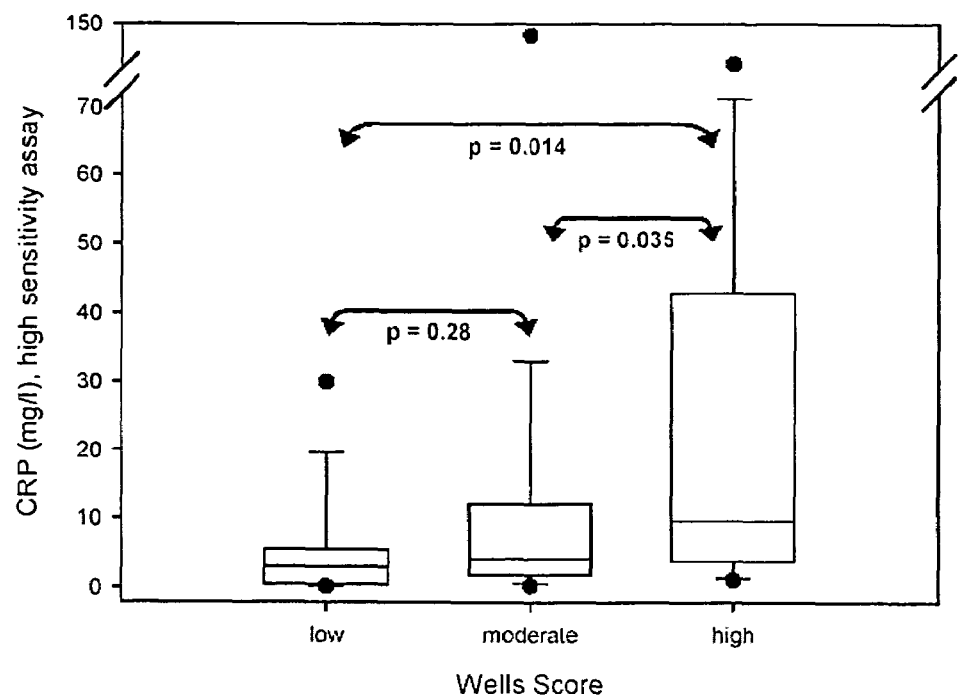

COMBINATION OF CRP AND D-DIMER FOR IN VITRO DIAGNOSIS OF DEEP VENOUS THROMBOSIS (DVT)

The present invention relates to an in vitro diagnostic method for patients with suspected deep venous thrombosis wherein by combined testing of patients' samples for D-dimer and CRP both the sensitivity and the negative predictive value of DVT diagnostics can be increased up to 100%.

Venous thrombosis is related to an inflammatory process that includes an early infiltration of the vein wall by neutrophils and an early increase in proinflammatory cytokines[1]. More specifically, recent results suggest important roles for IL-10[2,3] and P-selectin[4,5] in the regulation of this inflammation. Earlier reports on increased C-reactive protein (CRP) concentrations in acute venous thrombosis[6] have been contested[7,8]. Recently, so called "high sensitivity" (hs) assays were introduced to the clinical laboratory allowing reliable determination of CRP in a low to very low concentration range[9]. In patients with coronary artery disease, measuring hsCRP allows risk stratification for future cardiovascular events[10,11]. Therefore, research has mainly focused on the use of hsCRP as a risk marker for acute coronary syndromes[12].

Current diagnostic strategies for patients with suspected deep venous thrombosis usually combine the assessment of clinical probability[13] with D-dimer measurement; this approach identifies patients who need further diagnostic work-up[14]. The diagnostic accuracy of such an approach obviously depends on the quality of the D-dimer assay used[15]. Although the quality of modern, automated and quantitative D-dimer assays have been greatly enhanced over the last years, sensitivities and negative predictive values have not reached 100%[16]. Thus, an additional imaging procedure is deemed necessary to reliably exclude DVT in patients with high clinical probability[17]. Serial imaging procedures have been shown to be less cost effective as compared to initial D-dimer quantification followed by imaging in case of abnormal D-dimer concentrations[18]. Today's strategy for the initial work-up in patients with suspected DVT is based on the exclusion of the disease. Therefore, sensitivity and the negative predictive value (NPV) are the most important parameters of such an approach.

Thus, there is a need to further improve the diagnosis of DVT by increasing sensitivity and specificity of in vitro diagnostic methods in order to avoid time consuming and costly serial imaging procedures as much as possible.

Surprisingly the present inventors have found that by combined testing for D-dimer and C-reactive protein (CRP) both the sensitivity and the negative predictive value of DVT diagnostics can be increased up to 100%.

Therefore, the present invention relates to a method for the diagnostic exclusion of the presence of DVT in a patient at risk, comprising the following steps:
(a) testing of a liquid sample from said patient for with a reagent for the detection of D-dimer;
(b) evaluation of the test result:
  (i) if the D-dimer concentration is found to be equal to or above a predefined cut-off value, DVT is not excluded with said patient;
  (ii) if the D-dimer concentration is found to be below the said cut-off value, further testing according to (c) is performed:
(c) testing of a liquid sample from said patient with a reagent for the detection of C-reactive protein (CRP);
(d) evaluation of the test result: if the CRP-concentration is found below a predefined cut-off value, DVT is excluded with said patient.

D-dimer and CRP may be assayed for using different immunoassay test principles known to the skilled person such as turbidimetry, nephelometry, particle enhanced turbidimetry, particle enhanced nephelometry, latex agglutination, ELISA and all other conceivable immunochemical or immunohistochemical test methods. These and other detection methods are described, for example, in "Labor und Diagnose", ed. L. Thomas, TH-Books Verlagsgesellschaft mbH, Frankfurt, 1998, chapter 60, or in "Laboratory Techniques in Biochemistry and Molecular Biology—An Introduction to Radioimmunoassay and Related Techniques", ed. T. Chard, Elsevier, Amsterdam, 1987.

CRP detectable at low concentrations is often referred to as high sensitivity CRP (hsCRP), a term which will also be used below.

Suitable cut-off values may be defined by those skilled in the art individually for the D-dimer assay and the CRP assay based on well-known procedures. As an example, the following procedure may be applied: samples from a number of patients diagnosed with DVT, e.g. based on imaging procedures, and a number of probands not diseased with DVT may be tested for D-dimer and CRP; by evaluation of the test results obtained by each of the assays based on different cut-off values and combination of the results for D-dimer with those of CRP, that combination of cut-off values by which the negative samples are excluded whereas the positive sampled are not excluded, may be regarded as diagnostically useful.

A preferred embodiment of the present invention is the method for the diagnostic exclusion of the presence of DVT in a patient at risk as described above wherein D-dimer is tested for by a particle enhanced turbidimetric assay applying a cut-off-value at approximately 0.5 mg/l.

Another preferred embodiment of the present invention is the method for the diagnostic exclusion of the presence of DVT in a patient at risk as described above wherein CRP is tested for by a particle enhanced nephelometric assay applying a cut-off-value at approximately 4 mg/l.

An even more preferred embodiment of the present invention is the method for the diagnostic exclusion of the presence of DVT in a patient at risk as described above wherein D-dimer is tested for by a particle enhanced turbidimetric assay applying a cut-off-value at approximately 0.5 mg/l and CRP is tested for by a particle enhanced nephelometric assay applying a cut-off-value at approximately 4 mg/l.

In order to check the diagnostic efficiency of the method according to the present invention, DVT was demonstrated in 40 of 87 outpatients evaluated (distal DVT in 10, proximal DVT in 30 patients). HsCRP was significantly increased in patients with DVT (median 11.75 mg/l vs. 3.4 mg/l, p=0.0003) but was not different in patients with proximal or distal DVT. HsCRP concentrations were independent of gender but did show a weak correlation to age in patients without DVT (r=0.36, p=0.013). HsCRP values>4 mg/l predicted high probability Wells' scores (Odds Ratio 2.62, 95% Cl 1.01-6.82) and DVT (Odds Ratio 3.41, 95% Cl 1.36-8.53). Combining D-dimer (cut-off 0.5 mg/l) and hsCRP (cut-off 4 mg/l) according to the method of the present invention surprisingly maximized the sensitivity and negative predictive value (100% each) and increased specificity and positive predictive value at the same time.

In the following the method according to the present invention is described in more detail including experimental details. None of these details may be regarded as limiting the present invention in any way.

The present invention is further described in the patent claims.

DETAILED DESCRIPTION AND EXPERIMENTS

Patients and Methods

Patients

A detailed description of the patient population evaluated has been published elsewhere[20]. The study was approved by the local ethics committee and patients included had given their informed consent. In brief, consecutive patients referred for the work-up of a possible deep venous thrombosis (DVT) were included; patients were excluded if they had received any anticoagulant therapy for more than 24 hours prior to study enrollment; if they were hospitalised during the 3 days preceding study enrollment; or if a pregnancy was known. Pre-test probability was then determined according to Wells et al.[13], allowing distinction of "high", "moderate" and "low" probability groups. Thereafter, DVT was diagnosed or excluded by contrast venography or colour coded duplex sonography. If the work-up was negative, patients were followed up at 3 months. They were considered free of DVT if the initial work-up was negative and no signs of DVT occurred during the 3 months follow-up.

Assays

Upon presentation of the patient, citrated plasma was drawn, aliquoted and stored at −70° C. until used. D-dimer concentrations were determined using an automated, latex-enhanced, immunoturbidimetrical assay (Tinaquant D-dimer[16,20], run on a Hitachi 917 analyzer, Roche Diagnostics). A cut-off of 0.5 mg/l[16] was used for the exclusion of a DVT. CRP was measured with the Dade Behring high sensitivity CRP (hsCRP) assay[9,21], run on a BN II nephelometer (Dade Behring).

Statistics

A Receiver Operating Characteristics (ROC) Curve for hsCRP to predict DVT was plotted. HsCRP levels were correlated to age, gender, D-dimer concentration and Wells score (Spearman Rank Order). Median hsCRP levels in patients with and without DVT and in patients with low, moderate and high probability Wells score were compared (Mann-Whitney Test). For hsCRP levels above the cut-off, Odds Ratios for the presence of a high probability score and a DVT were calculated. SigmaStat (Version 2.0, SPSS, Chicago, USA) and MedCalc (Version-5-5.0, Medcalc Software, Mariakerke, Belgium; ROC Curve, Odds Ratios) software packages were used.

The following algorithm was used to evaluate the combined use of D-dimer and hsCRP: if Ddimer concentration was above the cut-off of 0.5 mg/l, presence of a DVT could not be excluded. If D-dimer was below 0.5 mg/l, the hsCRP concentration was also considered: if hsCRP was below the cut-off of 4 mg/l (see below), the patient was considered to be free of DVT, otherwise thrombosis was not excluded.

To compare the accuracy of using D-dimer versus D-dimer plus hsCRP, specificities and positive predictive values of both approaches were compared at identical (100%) sensitivity and NPV.

Results

Eighty-seven consecutive outpatients with suspected DVT were evaluated. Wells' scores were available for 76 patients, with 10, 31 and 35 patients having a low, moderate or high probability score, respectively. Contrast venography or colour-coded duplex ultrasonography revealed a DVT in 40 patients (10 distal DVT and 30 proximal DVT).

Patients without DVT had a significantly lower median hsCRP concentration (3.4 mg/l, 95% Cl 1.61-5.54 mg/l) compared to patients with DVT (11.75 mg/l, 95% Cl 6.10-29.70 mg/l, p=0.0003). HsCRP was not different in patients with proximal or distal DVT.

Median hsCRP concentrations were 3.01 mg/l for low, 4.31 mg/l for moderate and 9.7 mg/l for high probability Wells scores with significant differences between the high and the low to intermediate probability groups (FIG. 1). Crude Wells scores showed a weak correlation to hsCRP concentrations (r=0.363, p=0.002).

High sensitivity CRP concentrations were gender independent but showed a weak linear correlation to age in patients without DVT (r=0.36, p=0.013) but not patients with DVT (r=0.28, p=0.081).

There was a moderate correlation between D-dimer and hsCRP (r=0.550, p=<0.0001). The ROC curve for hsCRP (area under the curve 0.724, 95% Cl 0.617-0.814) shows the most accurate (minimal false negative and false positive results) cut-off at 6 mg/l. At that cut-off, however, sensitivity and NPV was suboptimal. Therefore, a hsCRP cut-off level of 4 mg/l was also evaluated, given that this level reflected half maximal specificity.

High sensitivity CRP values>4 mg/l predicted high probability Wells' scores (Odds Ratio 2.62, 95% Cl 1.01-6.82) and DVT (Odds Ratio 3.41, 95% Cl 1.36-8.53).

Figure 2:
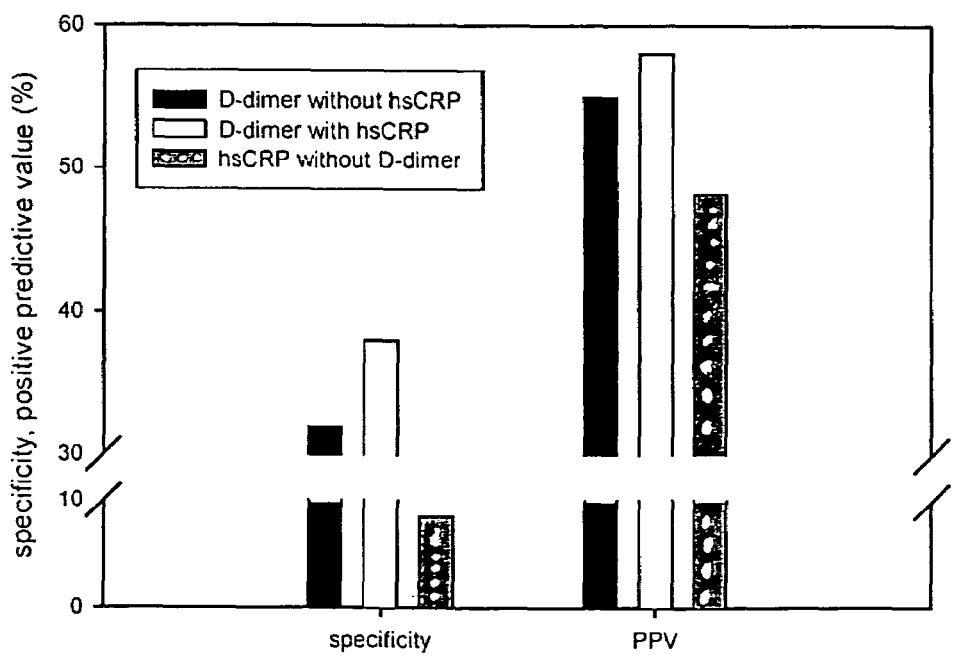

The diagnostic accuracy for D-dimer plus hsCRP was higher than for D-dimer alone (specificity and positive predictive value (PPV) were increased by 6% and 3% when compared at 100% sensitivity and 100% NPV, see FIG. 2), but the exclusion rate was somewhat lower (21% vs. 29%).

Employing the above outlined algorithm (i.e. to consider hsCRP only if D-dimer is below cut-off), consideration of hsCRP concentrations would have been necessary in 30% of patients evaluated in this study.

Discussion of the Results

In patients with coronary artery disease, the presence of a (low level) inflammation—as quantified by hsCRP assays—distinguishes between high-risk and non-high-risk patients, e.g. for recurrent acute coronary syndromes[12]. Consequently, inflammation as part of the disease is now being targeted in intervention trials[22].

Thrombosis in the venous system also induces a low level inflammatory response[1]. We postulated that the degree of inflammation in such patients could be related to the clinical picture as assessed by the Wells score[13] and therefore correlated hsCRP concentrations with this score. Patients with hsCRP above cut-off (4 mg/l) were more likely to have high probability Wells scores and DVT with Odds ratios of 2.62 and 3.41. Patients with DVT have significantly higher hsCRP concentrations than those without DVT. Others have reported[23] or refuted[24] that measuring CRP might be of value in the work-up of patients with suspected DVT. However, the use of high sensitivity CRP assays in this setting has not been investigated, neither on its own nor in combination with D-dimer measurements.

When combining D-dimer (cut-off 0.5 mg/l) and hsCRP (cut-off 4 mg/l) measurements, sensitivity and NPV for DVT were increased to 100% each, yielding an exclusion rate of 21%. Theoretically, 100% sensitivity and NPV can also be reached by simply lowering the D-dimer cut-off level, which would suggest that hsCRP does not truly add to improving diagnostic accuracy. To evaluate this question, we calculated the specificity and PPV of the D-dimer assay alone (i.e. without hsCRP) at a cut-off level that allows 100% sensitivity and 100% NPV (i.e. 0.32 mg/l). We then compared these results to specificity and PPV of the combined approach (D-dimer, cut-off 0.50 mg/l plus hsCRP, cut-off 4 mg/l). We found that specificity and the PPV increased with use of the combined approach (FIG. 2). This shows that including hsCRP in the combined approach truly adds to the accuracy of the D-dimer assay.

These results demonstrate that a combination of D-dimer and hsCRP—if both below the respective cut-off—may be used to exclude the presence of a DVT. Thus, since hsCRP levels correlate with the clinical presentation as assessed by the Wells' score, it seems that a combination of D-dimer and hsCRP possibly allows to assess patients by biochemical markers only—and thus to abrogate the need for labour- and time-intensive ultrasound and follow-up exams in a sizeable portion of patients.

From our data, we conclude that hsCRP can be used as a new diagnostic tool in the work-up of patients with suspected DVT. In combination, it maximizes sensitivity and negative predictive value (to 100% each) of D-dimer testing while adding to specificity and positive predictive value at the same time. The degree of low level inflammation at presentation as assessed by hsCRP correlates with the Wells score and describes the risk for the presence of a DVT.

REFERENCES

1. Wakefield T W, Strieter R M, Wilke C A, Kadell A M, Wrobleski S K, Burdick M D, Schmidt R, Kunkel S L, Greenfield L J. Venous thrombosis-associated inflammation and attenuation with neutralizing antibodies to cytokines and adhesion molecules. Arterioscler Thormb Vasc Biol. 1995; 15:258-68.
2. Henke P K, DeBrunye L A, Strieter R M, Bromberg J S, Prince M, Kadell A M, Sarkar M, Londy F, Wakefield T W. Viral IL-10 gene transfer decreases inflammation and cell adhesion molecule expression in a rat model of venous thrombosis. J Immunol. 2000; 164:2131-41.
3. Downing L J, Strieter R M, Kadell A M, Wilke C A, Austin J C, Hare B D, Burdick M D, Greenfield L J, Wakefield T W. IL-10 regulates thrombus-induced vein wall inflammation and thrombosis. J Immunol. 1998; 161:1471-6.
4. Myers D D, Jr., Schaub R, Wrobleski S K, Londy F J, 3rd, Fex B A, Chapman A M, Greenfield L J, Wakefield T W. P-selectin antagonism causes dose-dependent venous thrombosis inhibition. Thor Haemost. 2001; 85:423-9.
5. Wakefield T W, Strieter R M, Schaub R, Myers D D, Prince M R, Wrobleski S K, Londy F J, Kadell A M, Brown S L, Henke P K, Greenfield L J. Venous thrombosis prophylaxis by inflammatory inhibition without anticoagulation therapy. J Vasc Surg. 2000; 31:309-24.
6. Jossang B, Runde I. Diagnostic value of C-reactive protein and D-dimer in deep venous thrombosis. Tidsskr Nor Laegeforen. 1992; 112:1153-5.
7. Wong N A, Laitt R D, Goddard P R, Virjee J. Serum C reactive protein does not reliably exclude lower limb deep venous thrombosis. Thor Haemost. 1996; 76:816-7.
8. Maskell N A, Butland R J. A normal serum CRP measurement does not exclude deep vein thrombosis. Thor Haemost. 2001; 86:1582-3.
9. Roberts W L, Sedrick R, Moulton L, Spencer A, Rifai N. Evaluation of four automated high-sensitivity C-reactive protein methods: implications for clinical and epidemiological applications. Clin Chem. 2000; 46:461-8.
10. Ridker P M. High-sensitivity C-reactive protein: potential adjunct for global risk assessment in the primary prevention of cardiovascular disease. Circulation. 2001; 103:1813-8.
11. Haverkate F, Thompson S G, Pyke S D, Gallimore J R, Pepys M B. Production of Creactive protein and risk of coronary events in stable and unstable angina. European Concerted Action on Thrombosis and Disabilities Angina Pectoris Study Group. Lancet. 1997; 349:462-6.
12. Ridker P M, Rifai N, Pfeffer M A, Sacks F M, Moye L A, Goldman S, Flaker G C, Braunwald E. Inflammation, pravastatin, and the risk of coronary events after myocardial infarction in patients with average cholesterol levels. Cholesterol and Recurrent Events (CARE) Investigators. Circulation. 1998; 98:839-44.
13. Wells P S, Anderson D R, Bormanis J, Guy F, Mitchell M, Gray L, Clement C, Robinson K S, Lewandowski B. Value of assessment of pretest probability of deep-vein thrombosis in clinical management. Lancet. 1997; 350: 1795-8.
14. Perrier A, Desmarais S, Miron M J, de Moerloose P, Lepage R, Slosman D, Didier D, Unger P F, Patenaude J V, Bounameaux H. Non-invasive diagnosis of venous thromboembolism in outpatients. Lancet. 1999; 353:190-5.
15. Kovacs M J, MacKinnon K M, Anderson D, O'Rourke K, Keeney M, Kearon C, Ginsberg J, Wells P S. A comparison of three rapid D-dimer methods for the diagnosis of venous thromboembolism. Br J Haematol. 2001; 115:140-4.
16. Janssen M C, Heebels A E, de Metz M, Verbruggen H, Wollersheim H, Janssen S, Schuurmans M M, Novakova I R. Reliability of five rapid D-dimer assays compared to ELISA in the exclusion of deep venous thrombosis. Thor Haemost. 1997; 77:262-6.
17. Kraaijenhagen R A, Lensing A W, Lijmer J G, Prandoni P, Prins M H, Ginsberg J S, Buller H R. Diagnostic strategies for the management of patients with clinically suspected deep-vein thrombosis. Curr Opin Pulm Med. 1997; 3:268-74.
18. Perone N, Bounameaux H, Perrier A. Comparison of four strategies for diagnosing deep vein thrombosis: a cost-effectiveness analysis. Am J Med. 2001; 110:33-40.
19. Wakefield T W, Strieter R M, Prince M R, Downing L J, Greenfield L J. Pathogenesis of venous thrombosis: a new insight. Cardiovasc Surg. 1997; 5:6-15.
20. Fünfsinn N, Caliezi C, Demarmels-Biasiutti F D, Korte W, Z'Brun A, Baumgartner I, Ulrich M, Cottier C, Lämmle B, Wuillemin W A. Rapid D-dimer testing and pre-test clinical probability in the exclusion of deep venous thrombosis in symptomatic outpatients. Blood Coagul Fibrinolysis. 2001; 12:165-70.
21. Ledue T B, Weiner D L, Sipe J D, Poulin S E, Collins M F, Rifai N. Analytical evaluation of particle-enhanced immunonephelometric assays for C-reactive protein, serum amyloid A and mannose-binding protein in human serum. Ann Clin Biochem. 1998; 35 (Pt 6):745-53.
22. Albert M A, Staggers J, Chew P, Ridker P M. The Pravastatin Inflammation CRP Evaluation (PRINCE): Rationale and design. Am Heart J. 2001; 141:893-8.
23. Jossang B, Runde I. Diagnostic value of C-reactive protein and D-dimer in deep venous thrombosis. Tidsskr Nor Laegeforen. 1992; 112:1153-5.

24. Horney E, Lagerstedt C. Evaluation of analyses for exclusion of suspected thrombosis. Do not rely on the D-dimer test!. *Lakartidningen*. 1997; 94:4777-9.

Legends

FIG. 1: Median values and distribution of CRP measured with a hsCRP assay in patients suspected to have DVT in relationship to their clinical probability (Wells) scores 13. The differences in CRP between patients with either low or intermediate probability compared to patients with high probability are significant. A gradual increase in median CRP levels can be seen with increasing probability scores.

FIG. 2: Specificity and positive predictive value (PPV) for the D-dimer assay with and without combination with hsCRP measurements is displayed. The calculations were done at identical sensitivity and negative predictive value levels (100%). Addition of hsCRP to the work-up scheme increases specificity by 6% and the positive predictive value by 3%.

The invention claimed is:

1. A method for the diagnostic exclusion of the presence of deep venous thrombosis (DVT) in a patient at risk, comprising:
   (a) testing of a liquid sample from said patient with a reagent for the detection of D-dimer;
   (b) evaluating the test result:
      (i) if the D-dimer concentration is found to be equal to or above a predefined cut-off value, DVT is not excluded with said patient;
      (ii) if the D-dimer concentration is found to be below the said cut-off value, performing further testing according to (c):
   (c) testing of a liquid sample from said patient with a reagent for the detection of C-reactive protein (CRP);
   (d) evaluating the test result: if the CRP-concentration is found below a predefined cut-off value, DVT is excluded with said patient.

2. The method according to claim 1, wherein the liquid sample is serum, plasma or whole blood.

3. The method according to claim 1, wherein the reagents for the detection of D-dimer and for the detection of CRP are immunoassays.

4. The method according to claim 3, wherein the reagents for the detection of D-dimer and for the detection of CRP independently of each other are based on test principles chosen from: ELISA, turbidimetry, nephelometry, particle enhanced turbidimetry, particle enhanced nephelometry, and latex agglutination.

5. The method according to claim 1, wherein the predetermined cut-off value for D-dimer concentration is approximately 0.5 mg/l, and wherein the detection of D-dimer comprises a particle enhanced turbidimetric assay.

6. The method according to claim 1, wherein the predetermined cut-off value for CRP concentration is approximately 4 mg/l, and wherein the detection of CRP comprises a particle enhanced nephelometric assay.

7. The method according to claim 1, wherein the predetermined cut-off value for D-dimer concentration is approximately 0.5 mg/l, and wherein the detection of D-dimer comprises a particle enhanced turbidimetric assay, and further, wherein the predetermined cut-off value for CRP concentration is approximately 4 mg/l, and wherein the detection of CRP comprises a particle enhanced nephelometric assay.

* * * * *